US008515221B2

(12) United States Patent
Flanders et al.

(10) Patent No.: US 8,515,221 B2
(45) Date of Patent: Aug. 20, 2013

(54) SILICON OPTICAL BENCH OCT PROBE FOR MEDICAL IMAGING

(75) Inventors: Dale C. Flanders, Lexington, MA (US); James W. Getz, Harvard, MA (US); Walid A. Atia, Lexington, MA (US); Peter S. Whitney, Lexington, MA (US); Mark E. Kuznetsov, Lexington, MA (US)

(73) Assignee: Axsun Technologies, Inc., Billerica, MA (US)

( * ) Notice: Subject to any disclaimer, the term of this patent is extended or adjusted under 35 U.S.C. 154(b) by 641 days.

(21) Appl. No.: 12/693,181

(22) Filed: Jan. 25, 2010

(65) Prior Publication Data

US 2011/0182550 A1 Jul. 28, 2011

(51) Int. Cl.
*G02B 6/26* (2006.01)
(52) U.S. Cl.
USPC .......................................................... 385/31
(58) Field of Classification Search
None
See application file for complete search history.

(56) References Cited

U.S. PATENT DOCUMENTS

| | | | |
|---|---|---|---|
| 4,945,400 A | 7/1990 | Blonder et al. | |
| 5,692,084 A * | 11/1997 | Roff | 385/88 |
| 5,966,488 A * | 10/1999 | Miura et al. | 385/93 |
| 5,995,136 A | 11/1999 | Hattori et al. | |
| 6,335,522 B1 | 1/2002 | Shimada et al. | |
| 6,414,779 B1 | 7/2002 | Mandella et al. | |
| 6,419,810 B1 * | 7/2002 | Tanaka et al. | 205/73 |
| 6,530,698 B1 | 3/2003 | Kuhara et al. | |
| 6,717,753 B2 | 4/2004 | Sasaki | |
| 6,749,346 B1 | 6/2004 | Dickensheets et al. | |
| 7,416,674 B2 | 8/2008 | Coppeta | |
| 7,679,754 B2 | 3/2010 | Zuluaga | |
| 2009/0154872 A1 | 6/2009 | Sherrer et al. | |
| 2009/0190883 A1 | 7/2009 | Kato et al. | |
| 2010/0268058 A1 * | 10/2010 | Chen | 600/407 |

FOREIGN PATENT DOCUMENTS

| | | |
|---|---|---|
| JP | 2005018895 A | 1/2005 |
| WO | 2004078044 A1 | 9/2004 |
| WO | 2009076427 A1 | 6/2009 |

OTHER PUBLICATIONS

Awtar, Shorya, et al., "A compact mechanical probe for OCT based medical imaging that incorporates a MEMS scanner and a dynamically actuated objective lens," pp. 1-9, created Sep. 27, 2002.

(Continued)

*Primary Examiner* — Mike Stahl
(74) *Attorney, Agent, or Firm* — Houston & Associates, LLP

(57) ABSTRACT

An optical probe for emitting and/or receiving light within a body comprises an optical fiber that transmits and/or receives an optical signal, a silicon optical bench including a fiber groove running longitudinally that holds an optical fiber termination of the optical fiber and a reflecting surface that optically couples an endface of the optical fiber termination to a lateral side of the optical bench. The fiber groove is fabricated using silicon anisotropic etching techniques. Some examples use a housing around the optical bench that is fabricated using LIGA or other electroforming technology. A method for forming lens structure is also described that comprises forming a refractive lens in a first layer of a composite wafer material, such as SOI (silicon on insulator) wafers and forming an optical port through a backside of the composite wafer material along an optical axis of the refractive lens. the refractive lens is preferably formed using grey-scale lithography and dry etching the first layer.

20 Claims, 12 Drawing Sheets

(56) References Cited

OTHER PUBLICATIONS

Lan, Hsiao-Chin, et al., "Monolithic integration of elliptic-symmetry diffractive optical element on silicon-based 45° micro-reflector," Optics Express, vol. 17, No. 23, pp. 20938-20944, Nov. 9, 2009.

Xie, Tuqiang, et al., "GRIN lens rod based probe for endoscopic spectral domain optical coherence tomography with fast dynamic focus tracking," Optics Express, vol. 14, No. 8, pp. 3238-3246, Apr. 17, 2006.

Anonymous, "Combined Reflector and DOE couple light into or out of optical circuit," LaserFocusWorld, 1 page, Dec. 2009.

International Search Report mailed Sep. 6, 2011, from counterpart International Application No. PCT/US2011/022375, filed on Jan. 25, 2011.

International Preliminary Report on Patentability dated Aug. 9, 2012 from counterpart International Application No. PCT/US2011/022375, filed Jan. 25, 2011.

* cited by examiner

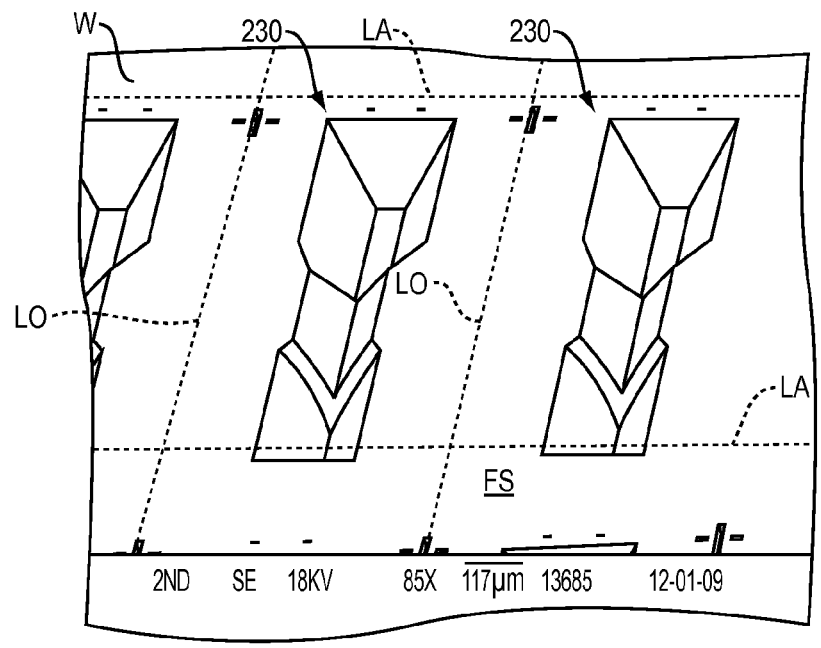
FIG. 16A
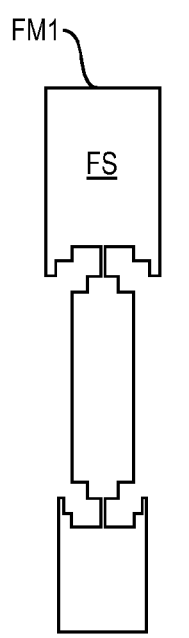 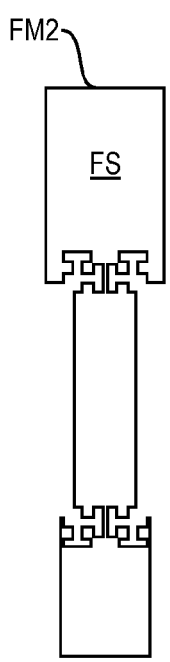
FIG. 16B          FIG. 16C

SILICON OPTICAL BENCH OCT PROBE FOR MEDICAL IMAGING

BACKGROUND OF THE INVENTION

Coherence analysis relies on the use of the interference phenomena between a reference wave and an experimental wave or between two parts of an experimental wave to measure distances and thicknesses, and calculate indices of refraction of a sample. Optical Coherence Tomography (OCT) is one example technology that is used to perform usually high-resolution cross sectional imaging. It is applied to imaging biological tissue structures, for example, on microscopic scales in real time. Optical waves are reflected from the tissue, in vivo, ex vivo or in vitro, and a computer produces images of cross sections of the tissue by using information on how the waves are changed upon reflection.

The original OCT imaging technique was time-domain OCT (TD-OCT), which used a movable reference mirror in a Michelson interferometer arrangement. In order to increase performance, variants of this technique have been developed using two wavelengths in so-called dual band OCT systems. In parallel, Fourier domain OCT (FD-OCT) techniques have been developed. One example uses a wavelength swept source and a single detector; it is sometimes referred to as time-encoded FD-OCT (TEFD-OCT) or swept source OCT. Another example uses a broadband source and spectrally resolving detector system and is sometimes referred to as spectrum-encoded FD-OCT or SEFD-OCT.

In parallel, Fourier domain OCT (FD-OCT) techniques have been developed. One example uses a wavelength swept source and a single detector; it is sometimes referred to as time-encoded FD-OCT (TEFD-OCT) or swept source OCT. Another example uses a broadband source and a spectrally resolving detector system and is sometimes referred to as spectrum-encoded FD-OCT or SEFD-OCT.

In scanning OCT, a light beam is focused onto the sample under test by a probe. Returning light is combined with light from a reference arm to yield an interferogram, providing A-scan or Z axis information. By scanning the sample relative to the probe, linear or two dimensional scans can be used to build up a volumetric image. One specific application involves the scanning of arteries, such as coronary arteries. The probe is inserted to an artery segment of interest using a catheter system. The probe is then rotated and drawn back through the artery to produce a helical scan of the inner vessel wall.

Traditionally, scanning OCT probes have been constructed from gradient refractive index (GRIN) lens and fold mirrors. Optical fibers are used to transmit optical signals to the probe at the distal end of the catheter system. The GRIN lens at the end of the fiber produces a collimated or focused beam of light and focuses incoming light onto the end of the optical fiber. The fold mirror couples to the GRIN lens to a region lateral to the probe.

SUMMARY OF THE INVENTION

In general, according to one aspect, the invention features an optical probe for emitting and/or receiving light within a body. The probe comprises an optical fiber that transmits and/or receives an optical signal, a silicon optical bench including a fiber groove running longitudinally that holds an optical fiber termination of the optical fiber and a reflecting surface that optically couples an endface of the optical fiber termination to a lateral side of the optical bench.

In embodiments, a lens structure is secured to the optical bench over the fold mirror surface. In some cases, the lens is anamorphic.

Further, the optical bench preferably comprises a blind groove section having a depth greater than at least part of the fiber groove with a distal end of the blind groove section forming the reflecting surface, which can be flat or curved. In the case of a curved reflecting surface, the optical power provided by the curved surface can be used to avoid the need for the lens structure.

In other aspects of embodiments, the fiber groove comprises a first depth section for fiber strain relief and a second depth section, the optical fiber comprising a sheathed portion in the first depth section of the optical bench and a bare portion in the second depth section of the optical bench.

In examples, a top bench is used over the fiber groove with the optical fiber termination being sandwiched between the top bench and the silicon optical bench. This top bench can have a fiber groove with a first depth section and a second depth section, a sheathed portion of the optical fiber being located in the first depth section of the top bench and a bare portion of the optical fiber being located in the second depth section of the top bench.

A housing is preferably provided around the bench. This housing comprises a optical port opposite the reflecting surface, through which the termination of the optical fiber is optically coupled to a region lateral to the probe.

In general according to another aspect, the invention features an optical probe for emitting and/or receiving light within a body. The probe comprises an optical fiber that transmits and/or receives an optical signal, a housing that contains an optical fiber termination of the optical fiber, the housing comprising at least a tubular section and a cap section, in which the cap section fits in a slot in the tubular section.

Preferably, an optical bench is provided in the slot of the tubular section and under the cap section, the optical fiber being held between the optical bench and the cap section. This cap section can comprise a groove running longitudinally on a backside, the optical fiber being held in the groove. An end section is useful for closing the slot at the distal end of the housing.

In general according to another aspect, the invention features an optical probe for emitting and/or receiving light within a body. This probe comprises an optical fiber that transmits and/or receives an optical signal and a housing that contains an optical fiber termination of the optical fiber, the housing comprising at least an electroformed tubular section.

In general according to still another aspect, the invention features a method for forming an optical probe for emitting and/or receiving light. This method comprises anisotropically etching wafer material to form grooves for holding optical fibers and singulating optical benches including the grooves from the wafer material.

Preferably blind grooves are formed in the wafer material, and coated to be reflective.

In general according to another aspect, the invention features a method for forming an optical probe for emitting and/or receiving light. This method comprises photolithographically patterning a resist layer; electroforming housings in the patterned resist layer, and inserting optical fiber terminations into the housings.

Preferably, the step of electroforming comprises electroplating. The method can also include electroforming cap sections that fit into slots in the housings along with installing optical benches in the housings, the optical fiber terminations being held on the optical benches.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 16A shows the bottom optical benches prior to singulation;

FIGS. 16B and 16C show exemplary frontside etch masks for forming the bottom optical benches.

DETAILED DESCRIPTION OF THE PREFERRED EMBODIMENTS

Figure 1:
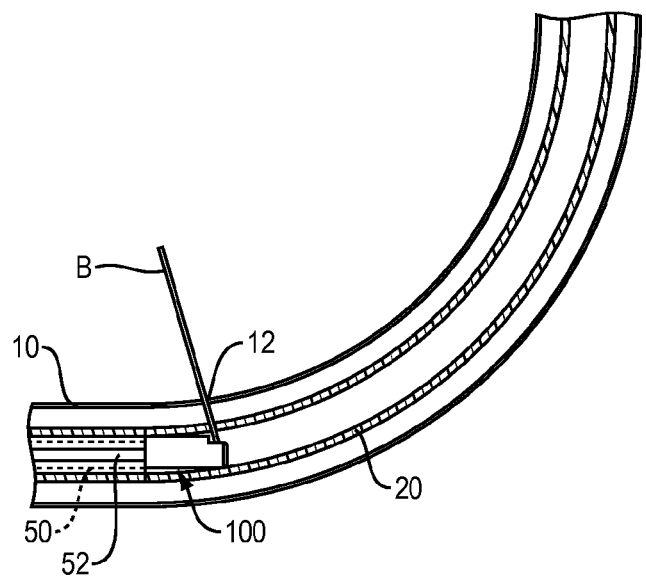
FIG. 1 shows the catheter with the probe in a lumen of a body.
Figure 2:
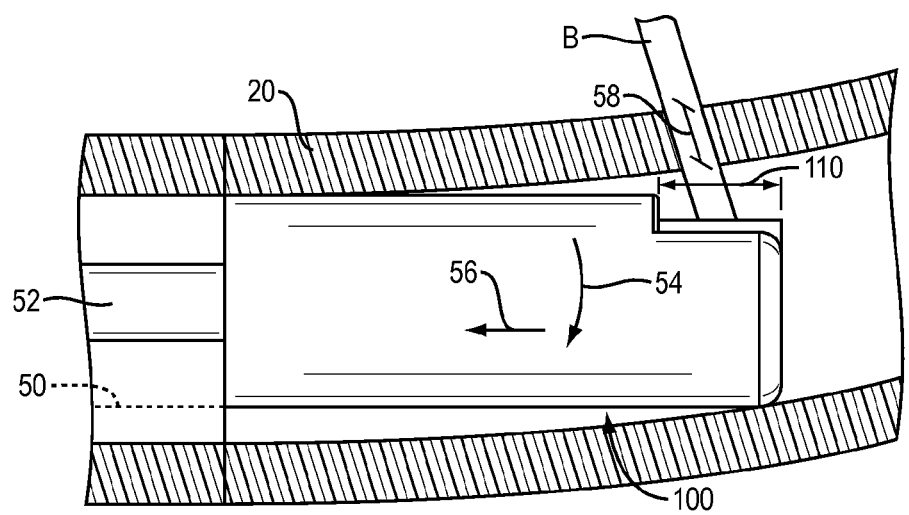
FIG. 2 is a detailed view of the probe in the sheath.

FIGS. 1 and 2 show a catheter system to which the present invention is applicable.

A catheter 50 is inserted into a lumen 10 of a body. In one typical example, the lumen 10 is a blood vessel, such as a coronary or carotid artery. In the illustrated example, the catheter 50 is located within a tubular and optically transmissive sheath 20 that protects the lumen. In more detail, the sheath is first inserted into the lumen and then the catheter 50 is introduced within the sheath.

A probe 100 is located at the end of the catheter 50. The probe 100 emits and/or receives an optical beam B in a direction that is lateral to the probe 100. The catheter 50 includes an optical fiber 52 extending longitudinally in the catheter 50. This transmits the light of beam B to and/or from the probe 100.

The beam B is emitted and/or collected through an optical port 110 of the probe 100. The beam is transmitted through the sheath 20, see reference 58. In the example of an OCT probe, the beam B is used to analyze the refractive index profile (A-scan) in the illuminated region 12 of the vessel wall 10. A complete scan of the inner wall of the vessel 10 is collected by helically scanning the probe 100 along a segment of the vessel 10. This is typically achieved by simultaneously rotating the probe 100, see arrow 54, while simultaneously withdrawing the probe 100 through the segment of interest, see arrow 56. The sheaths protect the vessel 10 during these scanning operations.

Figure 3:
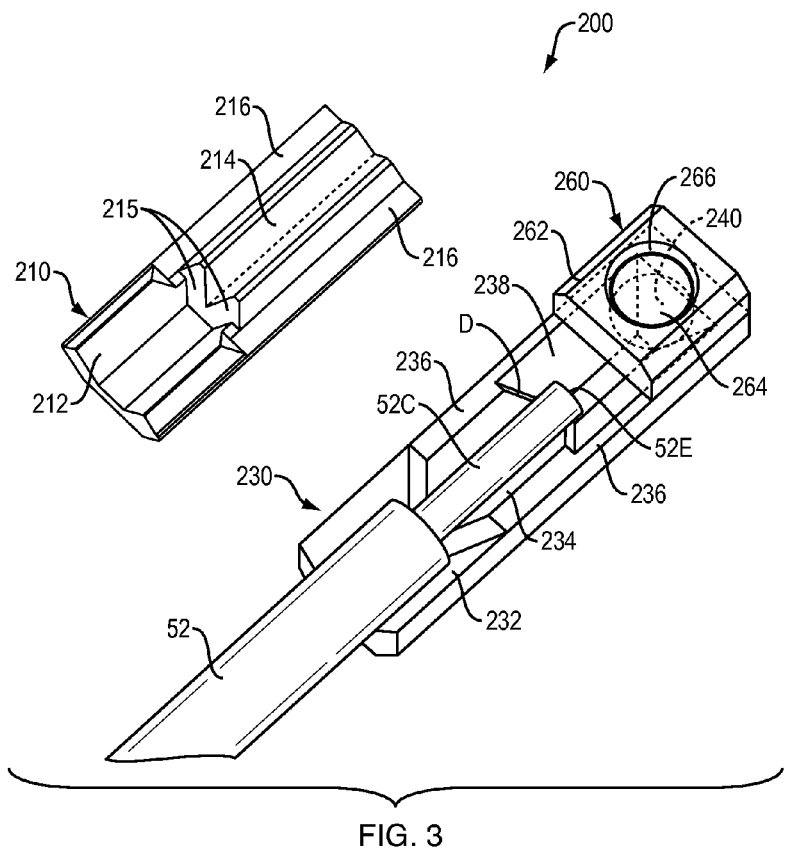
FIG. 3 is a perspective view of a bench system of the probe showing a top bench prior to installation on a bottom bench.

FIG. 3 shows an optical bench system 200 that is located within the probe 100 to optically couple the optical fiber 52 to a region that is lateral to the probe 100.

In more detail, the optical bench system 200 includes a top cap bench 210 and a bottom bench 230. In the preferred embodiment, these benches are fabricated from single crystal silicon or other similar material. The topographical features: V-grooves and ridges, of the bench system 200 are fabricated using a lithographic process and more specifically anisotropic etching techniques in which planes within the crystalline structure are etched at different rates to form the desired topography. The fabrication process many times also includes isotropic etching techniques such as dry etching, including reactive ion etching.

The top bench 210 fits on the bottom bench 230 such that the optical fiber 52 and especially the glass core 52C is held and clamped between the top cap bench 210 and the bottom bench 230.

To secure the fiber 52, the top cap bench 210 has a first fiber V-groove 212 extending in a longitudinal direction of the top cap bench 210. A second fiber V-groove 214 is aligned with the first fiber V-groove 212. The first V-groove 212 is deeper than the second fiber V-groove 214. The depth of the first V-groove 212 accommodates the optical fiber 52 including the outer polymer coating. The distal portion 52C of the optical fiber 52 is stripped of the outer coating to expose the glass core. As a consequence, the second fiber V-groove 214 of the top cap bench 210 is shallower than the first fiber V-groove 212.

On either lateral side of the second V-groove 214 are two engaging surfaces 216. In a lateral direction between the second V-groove 214, in the center of the top bench 210, and the engaging surfaces 216 at either edge of the top cap bench 210 are V-shaped ridges 215 that define the second V-groove 214 of the top cap bench 210.

The bottom bench 230 includes a first fiber V-groove 232. The depth of the first V-groove 232 of the bottom bench 230 is set to accommodate the coated optical fiber 52 and in this way corresponds to the first fiber V-groove 212 of the top cap bench 210. A second fiber V-groove 234 of the bottom bench 230 is aligned with the first fiber V-groove 232 along the central axis of the bottom bench 230. It is shallower than the first fiber V-groove 232 to capture the central glass core 52C of the stripped optical fiber 52.

At the longitudinal end of the second V-groove 234 of the bottom bench 230 is a blind V-groove or recess 238. In the typical embodiment, the blind V-groove 238 is deeper than the second V-groove 234 and has a depth that is similar to the first V-groove 232 of the bottom bench 230.

The blind V-groove 238 is further characterized by an end reflecting surface 240 at the longitudinal end of the blind V-groove and opposite the end facet or termination 52E of the optical fiber 52. In one example, the end reflecting surface 240 is coated with a reflecting layer such as a metal layer of gold or silver or a thin film multilayer dielectric mirror. In one example, the end reflecting surface 240 is planar. In another example it is curved to provide an optical power to focus the beam onto the end facet or termination 52E of the optical fiber 52 and/or collimate or focus the diverging beam from the end facet 52E.

On either lateral side of the first fiber V-groove 232, the second fiber V-groove 234, and the blind V-groove 238 are engaging surfaces 236 of the bottom bench 230. Upon assembly of the top cap bench 210 on the bottom bench 230, the engaging surfaces 216 of the top bench 210 sit on the engaging surfaces 236 of the bottom bench 230. Further, the V-shaped ridges 215 that define the second V-groove 214 of the top bench 210 fit within the second V-groove 234 of the bottom bench 230.

This assembly, cap bench/bottom bench, clamps the uncoated portion of the optical fiber 52 between the second fiber V-groove 214 of the top bench 210 and the second V-groove 234 of the bottom bench 230 providing precise alignment. The remaining matched surfaces are in close proximity and are locked in place with bonding material such as epoxy or solder.

The length of the stripped portion 52C of the optical fiber 52 is set relative to the length of the second V-groove 234 so that the end facet 52E projects slightly to the blind V-groove 238. As a result, in the example of the optical signal being emitted from the end of the optical fiber 52E, the signal is reflected off of the end reflecting surface 240 and directed to a region lateral to the benches 210, 230.

The increase in the V-groove size towards the turning mirror or end reflecting surface 240 helps in the subsequent bonding process. The size increase between the second fiber V-groove 234 and the blind V-groove 238 that forms wall D functions as a "wick stop" to prevent the epoxy from wicking around the end 52E of the fiber 52 during the bonding process.

In the current embodiment, a lens structure 260 is secured to the bottom optical bench over a portion of the blind V-groove 238 and specifically the end reflecting surface 240. The lens structure comprises a frame 262 that rests on the engaging surface 236 of the optical bench 230. The frame 262 has a central optical port 266. A lens 264 is secured or monolithically fabricated within this optical port 266. In the preferred embodiment, the lens 264 is a refractive anamorphic lens constructed from silicon or gallium phosphide and manufactured by photolithographic methods such as greyscale lithography and dry etching.

The lens is anamorphic to compensate for the optical power along one axis provided by the curvature of the sheath 20, see FIG. 1.

Figure 4:
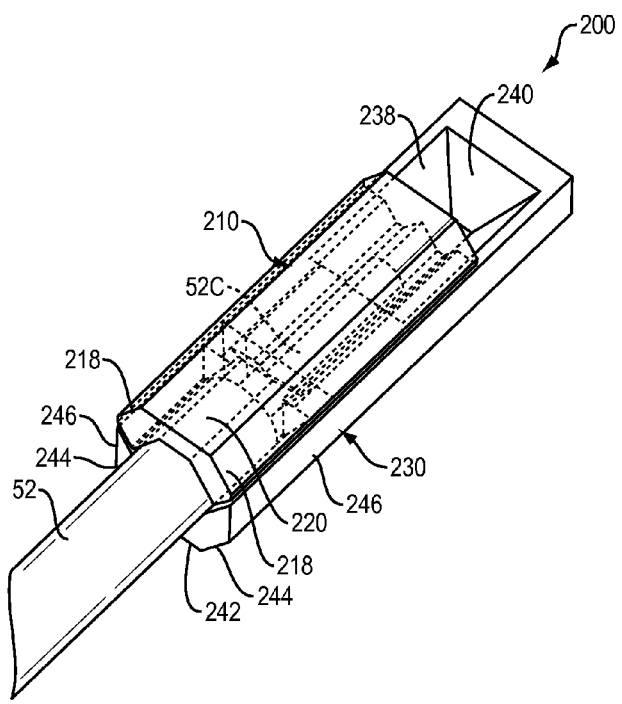
FIG. 4 is a perspective view of the bench system of the probe with the top bench shown in phantom installed on the bottom bench.

FIG. 4 illustrates the optical bench system in a partially assembled state. The top bench 210 is installed on the bottom bench 230 with the optical fiber 52 and the stripped portion 52C clamped between the top bench 210 and the bottom bench 230. The lens structure 260, however, is removed to illustrate the end reflecting surface 240, which has a triangular shape defined by the intersections with each wall side of the blind V-groove 238.

The outer cross-sectional profile of the assembled optical bench system 200 is octagonal in the illustrated embodiment. The cross-section profile is fabricated by backside V-groove etches in both the bottom bench 230 and the top cap bench 210 to form beveled edges when the V-grooves are used as cleave locations for singulation.

In more detail, the back side of the top cap bench 210 is characterized by a planar backface 220 and two beveled surfaces 218 on either side of the backface 220. The bottom bench 230 has a planar backface 242, two beveled surfaces 244 on either side of the backface 242 and two vertical side walls 246 that extend between the beveled surfaces 244 of the bottom bench 230 to the beveled surfaces 218 of the cap bench 210.

This octagonal profile and/or the beveled edges of the top bench (218) and bottom bench 244 approximate a circular cross-section. As a result, the bench system 200 able to be inserted into a circular bore of an outer housing with good contact with the inner walls of the bore.

Figure 5:
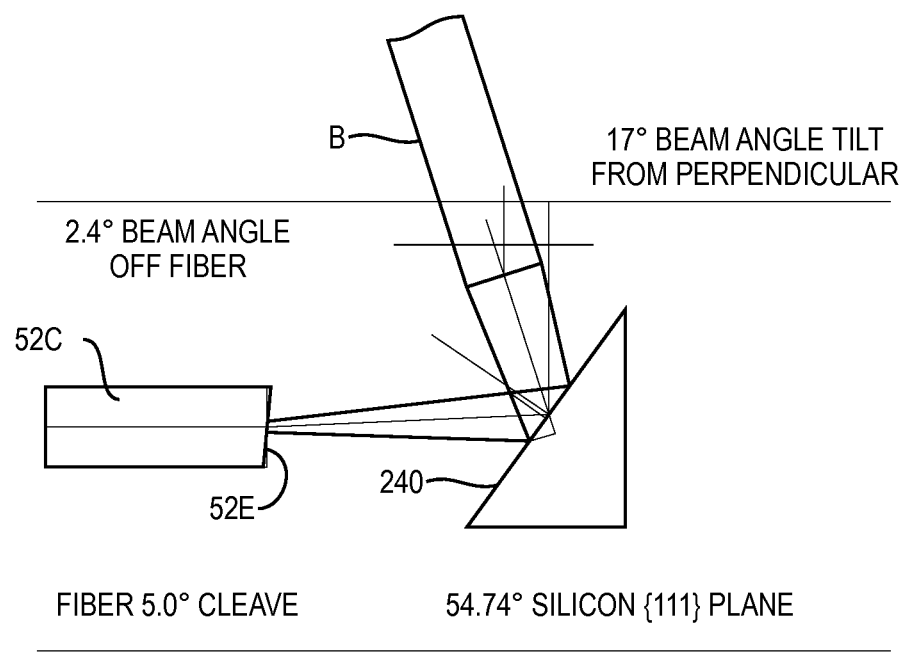
FIG. 5 is a schematic side plan view showing the beam being coupled to a region lateral to the probe.

FIG. 5 illustrates how end face 52E of the optical fiber 52 is coupled to the lateral portion of the probe 100.

In more detail, in one implementation, the end facet 52E of the optical fiber 52 is cleaved or polished at an angle of between 0 and 8°, for example, 5°, from perpendicular. The exact angle is chosen to optimize the optical reflectivity of the fiber end face 52E and is also dependent on the use of antireflective coatings on the end face. In more detail, the fiber end face 52E is coated with a thin film multilayer dielectric antireflective coating in one implementation to further control the optical reflectivity of the surface and allow optimization of the fiber end-face angle to favor the capabilities of the chosen fabrication method.

In a specific embodiment, the light exits from the optical fiber at an angle of 2.4° from horizontal. This light is transmitted to the end reflecting surface 240. With the end reflecting surface being fabricated from the silicon 111 plane, an angle of between 50° and 60° is formed. The angle will be precisely 54.74° with the crystal planes but there is a tolerance to the <100> plane when the wafer is diced out of the ingot. As a result, the beam B has an angle of about 10-20°, or 17° for example, from perpendicular as it exits the probe.

It should be noted that while this discussion is framed in the context of the light being emitted from the fiber 52 as beam B, the principle of optical reciprocity applies. Thus, the same analysis also applies to the situation where the light originates from a region lateral to the probe 100 and then is coupled into the optical fiber 52 using the end reflecting surface 240.

Figure 6:
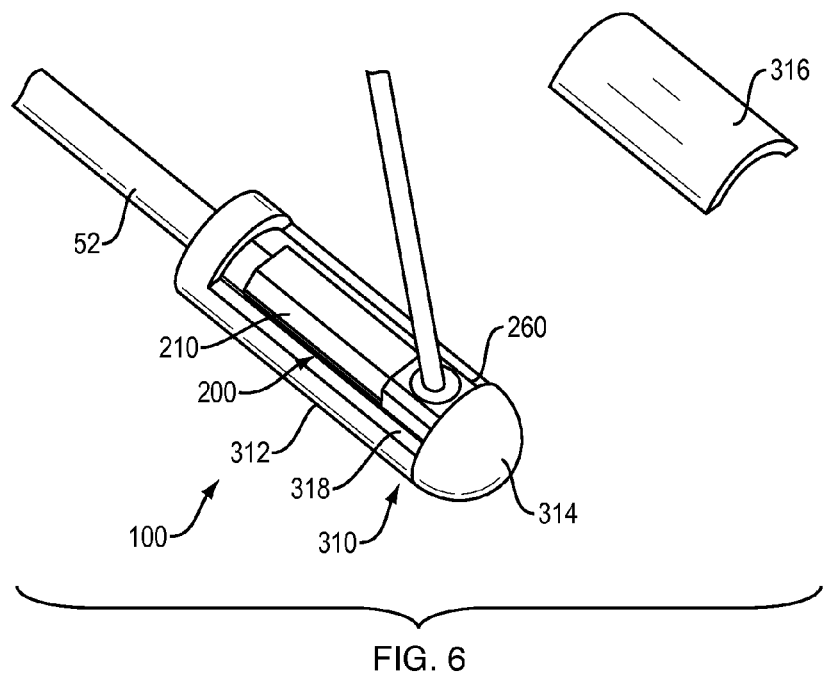
FIG. 6 is a perspective view of the probe with the bench system being installed within a housing, prior to installation of the cap portion.
Figure 7:
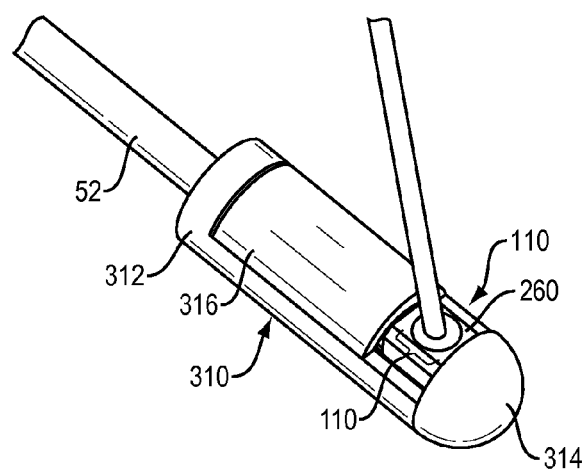
FIG. 7 is a perspective view of the probe with the bench system being installed within the housing and the cap portion of the housing installed over the bench system.

FIGS. 6 and 7 illustrate the optical bench system 200 of the probe 100 installed within an outer housing, according to a first embodiment.

In more detail, the optical bench system 200 with the optical fiber 52 is inserted into a hollow tubular outer housing assembly 310. In the illustrated embodiment, the outer housing assembly 310 comes in two pieces: a tubular section 312 with a distal dome-shaped nose 314 and a cap section 316. In assembly, the optical bench system 200 with the optical fiber 52 is slid into a cylindrical bore of the tubular section 312. It is typically bonded in place using an epoxy in the preferred embodiment. Then the cap section 316 is secured on to the tubular section 312.

The octagonal cross-sectional profile of the assembled optical bench system 200 ensures good a mechanical interface between the cylindrical inner bore of the tubular section 312 and the optical bench system 200.

One side of the tubular section 312 is open forming a window 318. The cap section 316 is sized to have the same cylindrical outer circumference as the tubular section 312 but is shorter in length than the window 318.

The assembled outer housing assembly is illustrated in FIG. 7 with the cap section 316 installed within the window 318. It leaves an optical port 110 over the lens structure 260 of the optical bench system 200 to accommodate transmission of the beam B.

Figure 8A:
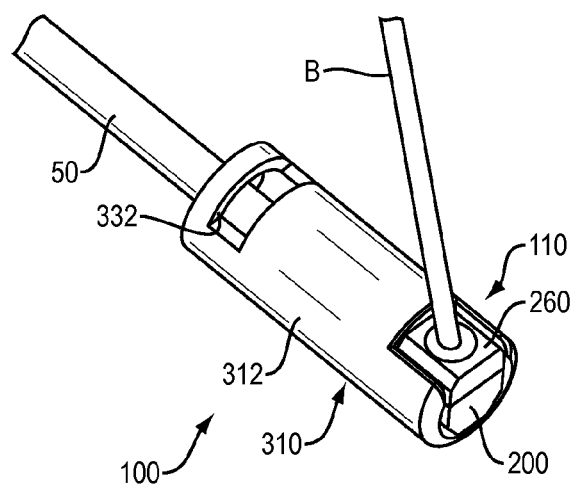
FIGS. 8A and 8B are perspective views of the probe showing two variants of a second embodiment of the housing.
Figure 8B:
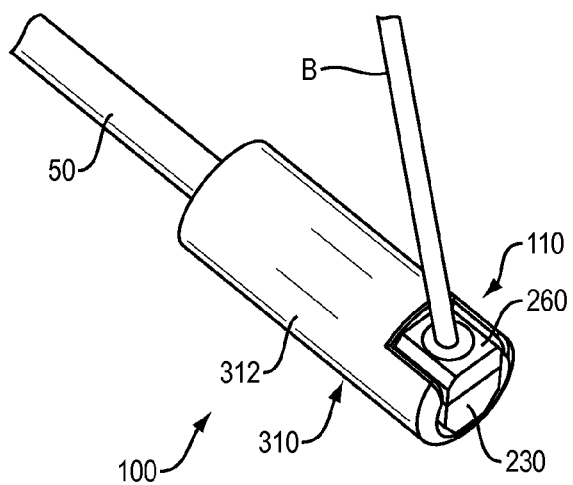

Figs. 8A and 8B illustrate two variants of a second embodiment of the outer housing 310. These embodiments have a smaller window section that is sized to the optical port 110. No cap section is required, instead, only the tubular section 312 is provided. In these embodiments, the bench system 200 is slid into the tubular section 312 until the lens structure 260 is aligned over the optical port 110.

The variants of FIGS. 8A and 8B differ in that the FIG. 8A version includes an epoxy port 332 in the tubular section 312. This allows an epoxy to be applied to the length of optical fiber exposed in the epoxy port 332 to improve strain relief for the fiber and ensure good mechanical joining between the optical bench system 200, optical fiber 52, and inner cylindrical bore in the tubular section 312.

Figure 9:
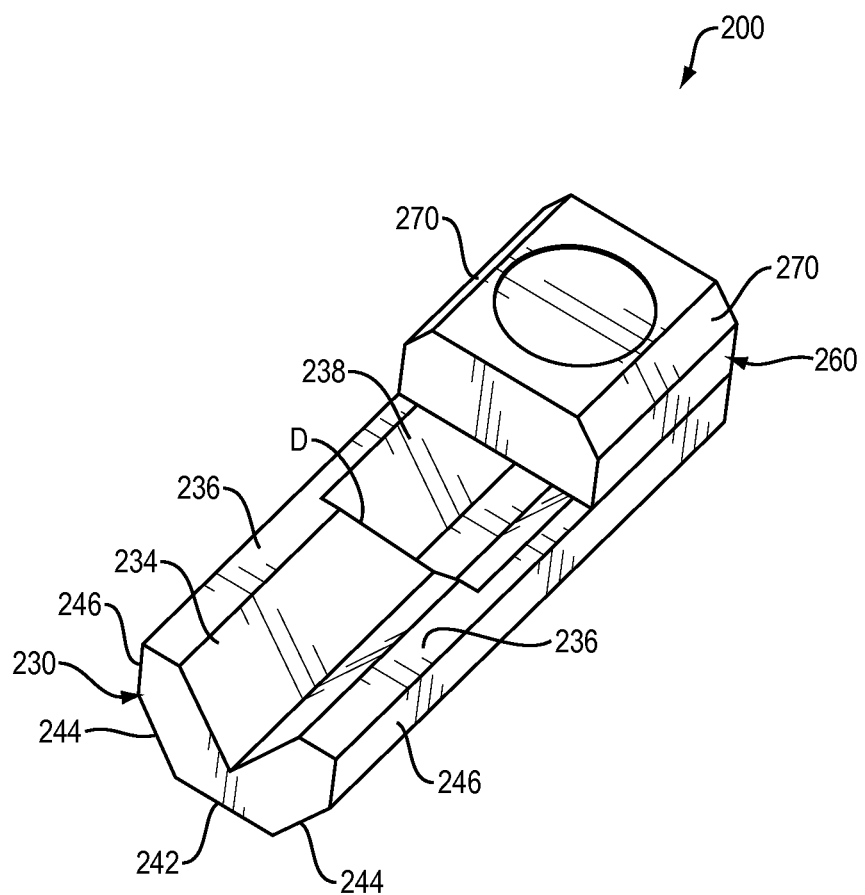
FIG. 9 is a perspective view of a second embodiment of the bench system of the probe.

FIG. 9 shows a second embodiment of the silicon optical bench system 200. In this version only a single, bottom silicon optical bench 230 is used, without a top optical bench. This is embodiment is further simplified in that a single fiber V-groove 234 is provided, into which the glass core of the optical fiber is secured.

Aligned with the single fiber V-groove 234 is a blind V-groove or recess 238. The blind V-groove 238 ends in the angled reflecting surface as described with respect to the first embodiment. Over the angled reflecting surface is the lens structure 260 as also described in the previous embodiment.

The outer cross-sectional profile of the assembled optical bench system 200 is also octagonal. The cross-section profile is fabricated by backside V-groove etches in both the bottom bench 230 and the lens structure 260 to form beveled edges when the V-grooves are used as cleave locations for singulation. In more detail, The bottom bench 230 has a planar backface 242, two beveled surfaces 244 on either side of the backface 242 and two vertical side walls 246 that extend between the beveled surfaces 244 of the bottom bench 230 to beveled surfaces 270 of lens structure 260.

Here also, the increase in the V-groove size towards the turning mirror or end reflecting surface 240 helps in the subsequent fiber bonding process. The size increase between the second fiber V-groove 234 and the blind V-groove 238 that forms wall D functions as a "wick stop" to prevent the epoxy from wicking around the end of the fiber.

This second embodiment has the advantage of being much simpler in construction. On the other hand, since only the glass core is secured to the optical bench system 200, there is less strain relief for the optical fiber.

Figure 10:
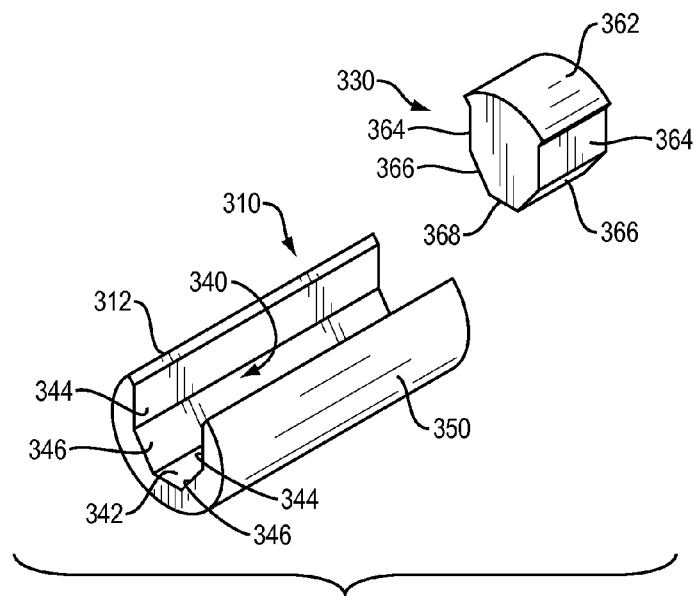
FIG. 10 is a perspective view of the third embodiment housing and end section, in an unassembled state.
Figure 11:
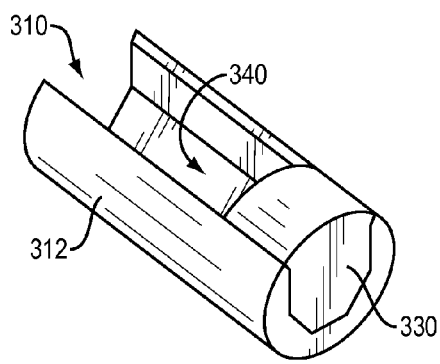
FIG. 11 is a perspective view of the housing and end section, according to a third embodiment, in an assembled state.
Figure 12:
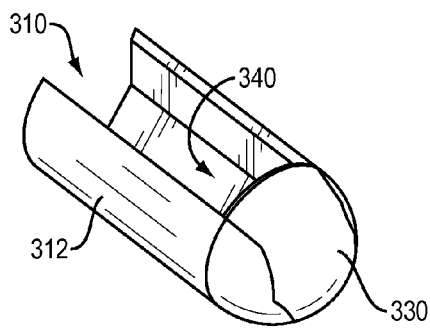
FIG. 12 is a perspective view of the housing and end section, according to a variant of the third embodiment.

FIGS. 10-12 show a third embodiment of the outer housing 310 that is compatible with the second embodiment of the optical bench system 200, shown in FIG. 9.

Referring to FIG. 10, in more detail, the third embodiment comprises a tubular section 312. The outer surface 350 of the tubular section has a generally cylindrical shape. The tubular section 312 has a longitudinally running slot 340. In cross-section, that longitudinally running slot 340 has vertically extending sidewalls 344 at the mouth of the slot. It further has a horizontal flat bottom 342. Angled or the V-groove-shaped sidewalls 346 link the vertical sidewalls 344 and the flat bottom 342 in the cross-section.

An end section 330 fits within the tubular section 312 and specifically within the longitudinal running slot 340. An outer wall 362 of the end section 330 forms a cylindrical section that completes the cylindrical shape of the outer housing 310 when the end section 330 is installed within the slot 340. The end section 330 further has vertical sidewalls 364, a flat bottom 368, and angled, V-groove sides 366 that correspond to the shape of the inner walls of the slot 340.

FIG. 11 shows the third embodiment of the housing 310 with the end section 330 installed within the slot 340 of the tubular section 312.

FIG. 12 shows a variant of the third embodiment of the housing 310. It has a dome shaped end section 330.

Figure 13:
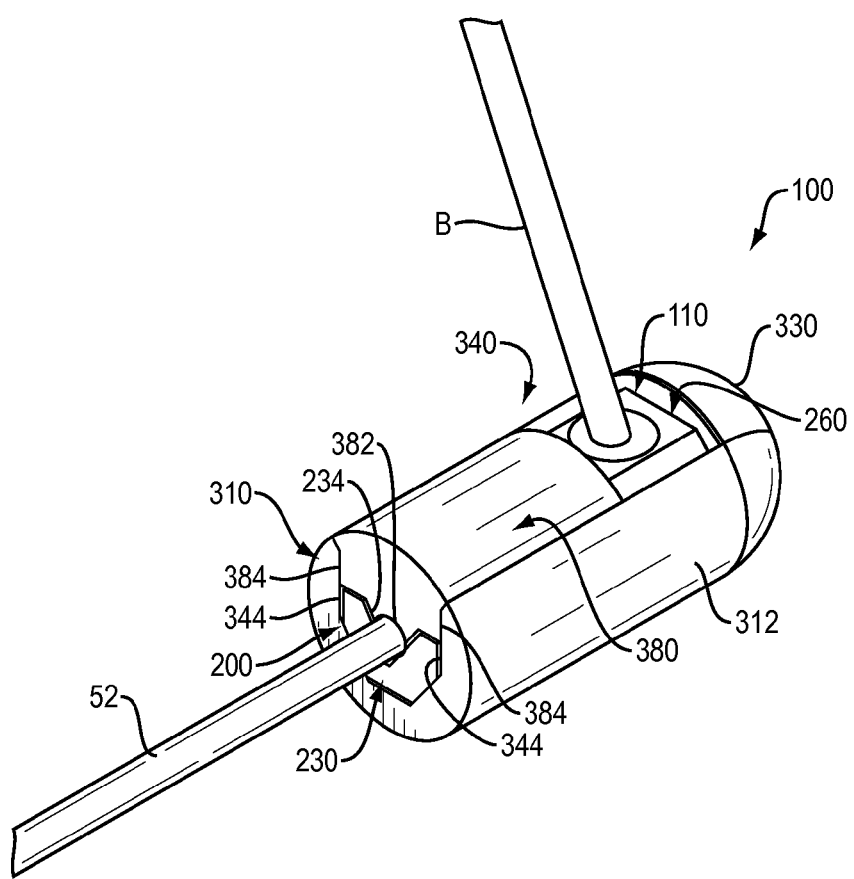
FIG. 13 is a perspective view of the probe showing a third embodiment of the housing with the second embodiment optical bench system.

FIG. 13 shows a fully assembled probe 100, utilizing the third embodiment of the housing 310 and the second embodiment of the optical bench system 200.

In more detail, the optical fiber 52 is installed within the fiber V-groove 234 of the bottom bench 230. The bottom bench 230 in turn is installed within the longitudinally running slot 340 of the tubular section 312 of the housing 310. Further, at the distal end of the longitudinally running slot 340, the end section 330 is installed within the slot 340.

A cap section 380 is installed in a slot 340 over at the bottom bench 230. The optical fiber 52 is clamped between the cap section 380 and the bottom bench 230. The cap section 380 has a cylindrical recess 382 in its cross section that engages the top of the optical fiber 52. Additionally, vertical sections 384 of the cap section 380 engage the corresponding vertical walls 344 of the tubular section 310. An optical port 110 is provided in the outer housing 310 over the lens structure 260 that is installed on the bottom bench 230. This port 110 is defined by a space between the cap section 380 and the end section 330 in the longitudinal directions and by the sides of the slot 340 in the lateral directions.

Preferably, the third embodiment of the housing 310 illustrated in FIGS. 10-13 is manufactured using the LIGA or related electroforming process. LIGA is an acronym for Lithographie, Galvanoformung, Abformung (Lithography, Electroplating, and Molding, in English) that represents a fabrication technology for high-aspect-ratio microstructures that generally have cross-sectionally constant profile, extrusions.

Figure 14A:
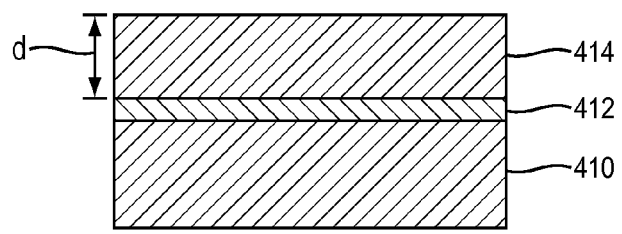
FIGS. 14A-14C are schematic side plan views showing an electroforming manufacturing process for the housings made using the LIGA process.
Figure 14B:
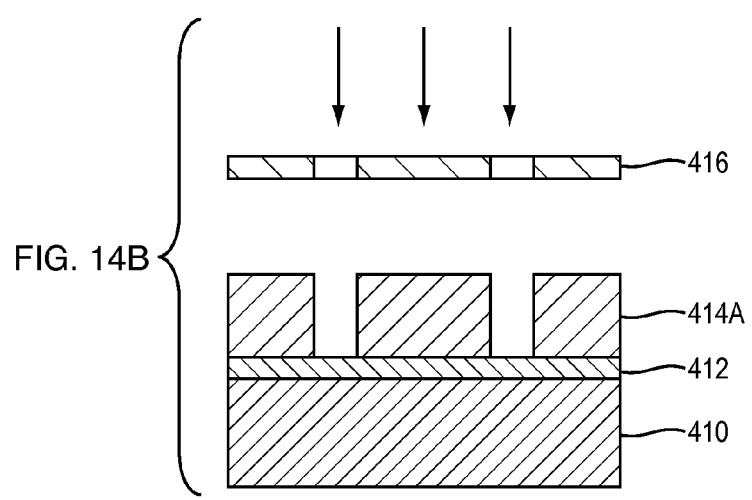
Figure 14C:
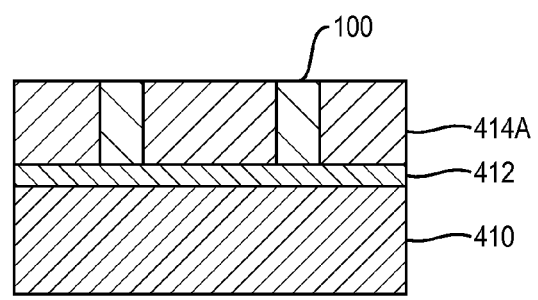

FIGS. 14A-14C are cross-sectional views showing the fabrication steps for the outer housing 310, end section 330 and the cap section 380 using the electroforming process.

Specifically, as illustrated in FIG. 14A, a thick PMMA (polymethylmethacrylate) or SU-8 resist layer 414 is bonded to a seed/release layer 412 on a substrate 410.

The depth d of the resist layer 414 determines the maximum thickness of the subsequently manufactured extrusion portion. As a result, the depth determines the length of the part: outer housing 310, end section 330 and the cap section 380.

FIG. 14B illustrates the next fabrication step in the outer housing 310, end section 330 and the cap section 380. Specifically, the thick resist layer 414 is patterned by exposure to collimated x-rays in the case of a PMMA resist or ultraviolet light in the case of SU-8. Specifically, a mask 416, which is either be a positive or negative mask having the desired pattern for the structure, is placed between the radiation source such as a synchrotron or UV light and the resist layer 414. The resist layer 414 is then developed into the patterned layer 414A as illustrated in FIG. 14B.

FIG. 14C shows the formation of the quasi-extrusion portion of the outer housing 310, end section 330 and the cap section 380. Specifically, in the preferred embodiment, the quasi-extrusion portion is formed via electroplating onto the seed layer 412 into the photolithographically formed mould of the patterned resist layer 414A. The preferred plating metal is nickel according to the present embodiment. Nickel alloys, such as a nickel-iron alloy, are used in other embodiments. Alternatively gold or a gold alloy is used in still other embodiments. Currently, alternative metal and alloys include: silver, silver alloy, nickel copper, nickel cobalt, gold cobalt and alloys laden with colloidal oxide particles to pin the microstructures.

Figure 15A:
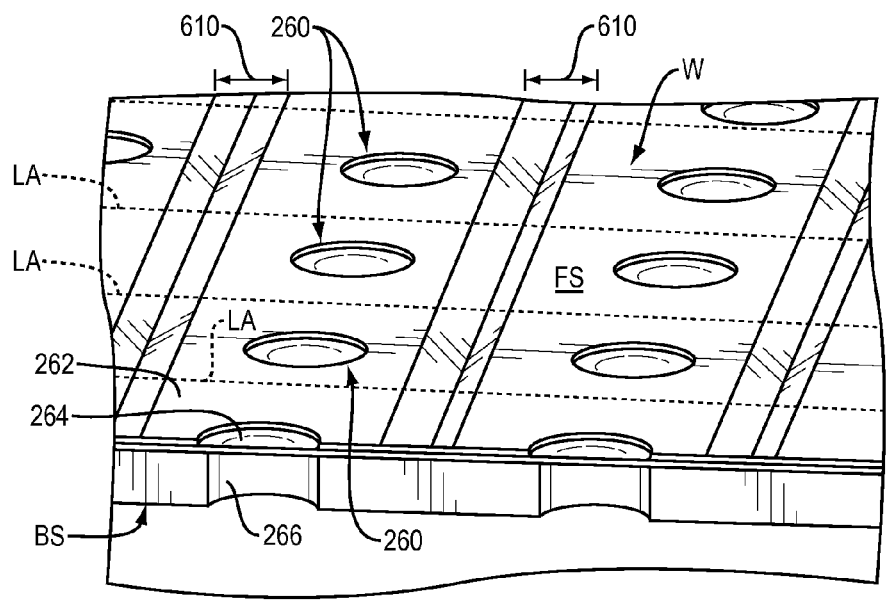
FIGS. 15A and 15B are perspective views of a wafer of lens structures, with the edge showing the lens structures in cross-section.
Figure 15B:
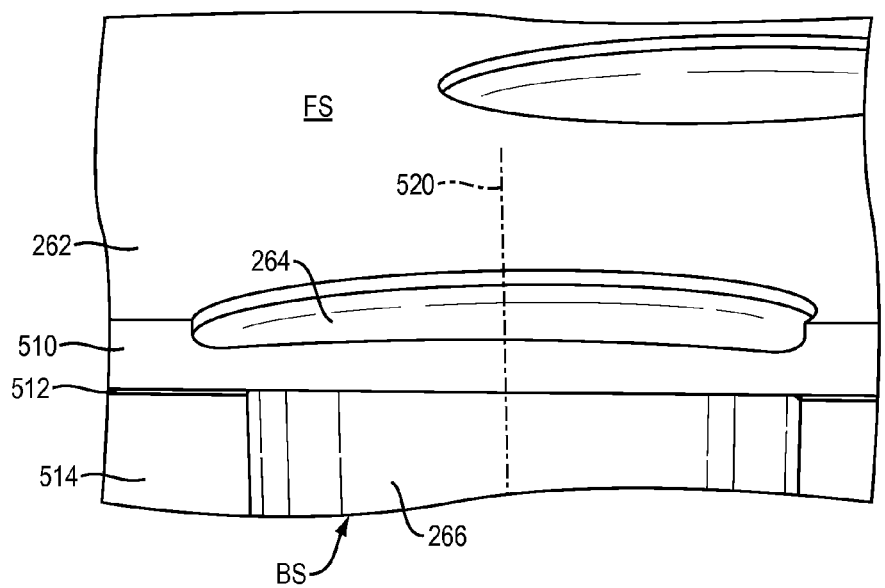

FIGS. 15A and 15B shows a wafer of lens structures including some of the lens structures in cross-section to illustrate the fabrication method of the lens structures 260.

In more detail, as shown in FIG. 15A, the lens structures 260 are mass produced in wafer material W. Each lens structure comprises the frame 262, which has a central optical port 266. The refractive lens 264 formed over the optical port 262.

The lenses 264 are fabricated from silicon or gallium phosphide and are preferably manufactured by photolithographic methods including grey-scale lithography and dry etching on the frontside FS of the wafer W. In other examples, the lenses are made using the CMP process disclosed in U.S. Pat. No. 7,416,674 B2, which is incorporated herein in its entirety by this reference.

As better shown in FIG. 15B, in the preferred embodiment, the wafer material W is a composite wafer, preferably silicon on insulator (SOI). The lens 264 is fabricated in the device wafer material 510. A buried oxide interlayer 512 separates the handle wafer material 514 from the device wafer material 510.

Handle wafer material 514 primarily functions as the frame and the mechanical support for the lens structure 260. In the preferred embodiment, the handle wafer is silicon wafer, the device layer has a thickness of 10-50 μm, currently 25 μm, and the buried oxide has a thickness 1-4 μm, currently 2 μm. The lens etch is roughly 5 μm deep at the deepest point.

The optical port 266 is fabricated using a backside etch into the backside BS of the handle wafer material 514 along a center optical axis 520 of the refractive lens 264. This backside etch is preferably a dry etch, reactive ion etch, that stops on a buried oxide layer 512, which separates the handle wafer material 514 from the device wafer material 510. A wet or dry etch is then used to remove the oxide at the bottom of the optical port 262 to expose the backside of the lens 264. Also in the preferred embodiment, antireflective dielectric coatings are preferably applied to the frontside FS and backside BS, specifically onto the lens 264.

In addition to the backside antireflective coatings, metal is preferably deposited on the backside BS to facilitate bonding to the bottom optical bench.

Referring back to FIG. 15A, the lens structures 260 are separated in a singulation process. In the preferred embodiment, along one axis, the V-grooves 610 are formed on the front side FS of the wafer W, in between the lenses 264 of the lens structures 260. These V-grooves 610 form the bevel edges 270 of the lens structures 260 on the lateral sides. The V grooves 610 also function as lines for cleaving the wafer to form the separate lines of lens structures. Lateral scribe lanes LA are used to separate the lines of lens structures 260 into individual singulated lens structures 260. A wet or dry etch along lanes LA is used in some embodiments to facilitate singulation.

FIG. 16A illustrates the formation of the separate bottom optical benches 230 on a single wafer using photolithographic/anisotropic etching. Specifically, in a single wafer W, lines of optical benches 230 are formed into the frontside FS of the wafer W. These optical benches 230 are then singulated into individual optical benches by cleaving along the lateral scribe lines LA and the longitudinal scribe planes LO.

FIGS. 16B and 16C illustrate exemplary etch masks FM1, FM2 for the anisotropic etches that are used to form the frontsides FS of the bottom optical benches 230. In more detail, the etch masks are used to photolithographically pattern a resist layer on the wafer material, which is then developed. The frontside of wafer is then exposed to a timed, wet, anisotropic etch process using buffer KOH, for example.

Figure 16D:
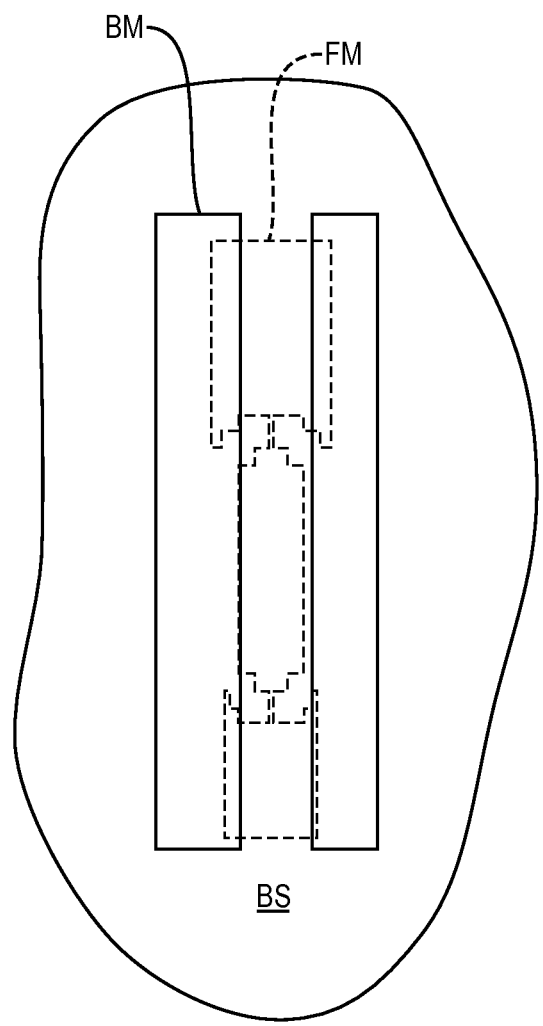
FIG. 16D shows an exemplary backside etch mask for forming the bottom optical benches.

FIG. 16D illustrates the relationship between the backside etch mask BM and the front side edge mask FM. In more detail, on the backside BS, the beveled edges of the bottom optical bench (see reference 244 in FIG. 4) are formed using a backside mask BM that has two exposed portions on either side of the mask used on the front side etch FM. The backside mask pattern BM forms to V-grooves on each lateral side that are used to form the beveled edges on the backside of the bottom optical benches.

While this invention has been particularly shown and described with references to preferred embodiments thereof, it will be understood by those skilled in the art that various changes in form and details may be made therein without departing from the scope of the invention encompassed by the appended claims.

What is claimed is:

1. An optical probe for emitting and/or receiving light within a body, the probe comprising:
   an optical fiber that transmits and/or receives an optical signal; and
   a silicon optical bench including a fiber groove running longitudinally that holds an optical fiber termination of the optical fiber and a reflecting surface that optically couples an endface of the optical fiber termination to a lateral side of the optical bench, wherein the optical bench further includes a blind groove having a depth greater than at least part of the fiber groove with a distal end of the blind groove forming the reflecting surface.

2. An optical probe as claimed in claim 1, further comprising a lens structure secured to the optical bench over the reflecting surface.

3. An optical probe as claimed in claim 2, wherein a lens in the lens structure is anamorphic.

4. An optical probe as claimed in claim 1, wherein the reflecting surface is flat.

5. An optical probe as claimed in claim 1, wherein the reflecting surface is curved.

6. An optical probe as claimed in claim 1, wherein the fiber groove comprises a first depth section for fiber strain relief and a second depth section, the optical fiber comprising a sheathed portion in the first depth section of the optical bench and a bare portion in the second depth section of the optical bench.

7. An optical probe as claimed in claim 1, further comprising a top bench over the fiber groove with the optical fiber termination being sandwiched between the top bench and the optical bench.

8. An optical probe as claimed in claim 7, wherein the top bench comprises a first fiber groove with a first depth section and a second fiber groove with a second depth section, a sheathed portion of the optical fiber being located in the first depth section of the top bench and a bare portion of the optical fiber being located in the second depth section of the top bench.

9. An optical probe as claimed in claim 8, further comprising a lens structure secured to the optical bench over a fold reflecting surface and next to the top bench.

10. An optical probe as claimed in claim 1, further comprising a housing surrounding the optical bench.

11. An optical probe for emitting and/or receiving light within a body, the probe comprising:
- an optical fiber that transmits and/or receives an optical signal;
- a silicon optical bench including a fiber groove running longitudinally that holds an optical fiber termination of the optical fiber and a reflecting surface that optically couples an endface of the optical fiber termination to a lateral side of the optical bench; and
- a housing surrounding the optical bench, wherein the housing comprises a optical port opposite the reflecting surface, through which the termination of the optical fiber is optically coupled to a region lateral to the probe.

12. An optical probe as claimed in claim 11, wherein the housing comprises a tubular section and a cap section, wherein the cap section fits in a slot in the tubular section.

13. An optical probe for emitting and/or receiving light within a body, the probe comprising:
- an optical fiber that transmits and/or receives an optical signal;
- a housing that contains an optical fiber termination of the optical fiber, the housing comprising at least a tubular section and a cap section, in which the cap section fits in a slot in the tubular section; and
- a lens structure in a window formed by part of the slot of the tubular section.

14. An optical probe as claimed in claim 13, further comprising a reflecting surface below the window.

15. An optical probe for emitting and/or receiving light within a body, the probe comprising:
- an optical fiber that transmits and/or receives an optical signal;
- a housing that contains an optical fiber termination of the optical fiber, the housing comprising at least a tubular section and a cap section, in which the cap section fits in a slot in the tubular section; and
- an optical bench in the slot of the tubular section and under the cap section, the optical fiber being held between the optical bench and the cap section.

16. An optical probe for emitting and/or receiving light within a body, the probe comprising:
- an optical fiber that transmits and/or receives an optical signal;
- a housing that contains an optical fiber termination of the optical fiber, the housing comprising at least a tubular section and a cap section, in which the cap section fits in a slot in the tubular section, wherein the cap section comprises a groove running longitudinally on a backside, the optical fiber being held in the groove, between the cap section and the tubular section; and
- an optical bench in the slot of the tubular section and under the cap section, the optical fiber being held between the optical bench and the cap section.

17. An optical probe for emitting and/or receiving light within a body, the probe comprising:
- an optical fiber that transmits and/or receives an optical signal;
- a housing that contains an optical fiber termination of the optical fiber, the housing comprising at least a tubular section and a cap section, in which the cap section fits in a slot in the tubular section;
- an optical bench in the slot of the tubular section and under the cap section, the optical fiber being held between the optical bench and the cap section; and
- an end section that closes the slot at the distal end of the housing.

18. An optical probe for emitting and/or receiving light within a body, the probe comprising:
- an optical fiber that transmits and/or receives an optical signal;
- a housing that contains an optical fiber termination of the optical fiber, the housing comprising at least an electroformed tubular section;
- an electroformed cap section that fits into a slot in the housing, wherein the cap section comprises a groove running longitudinally on a backside, the optical fiber being held in the groove, between the cap section and the tubular section; and
- an optical bench in the slot of the tubular section and under the cap section, the optical fiber being held between the optical bench and the cap section.

19. An optical probe as claimed in claim 18, wherein the housing is formed by electroplating.

20. An optical probe as claimed in claim 18, wherein the housing is formed by electroplating into a photolithographically formed mould.

* * * * *